United States Patent [19]

Takayama et al.

[11] 4,038,287

[45] July 26, 1977

[54] COMPOUNDS OF ALLANTOIN WITH BASIC AMINO ACIDS

[75] Inventors: Hirohide Takayama, Ogose; Kiyoshi Niino, Hidaka; Sigeo Fukuda, Kawagoe, all of Japan

[73] Assignee: Kawaken Fine Chemicals Co., Ltd., Tokyo, Japan

[21] Appl. No.: 676,134

[22] Filed: Apr. 12, 1976

[30] Foreign Application Priority Data

Apr. 21, 1975 Japan .................................. 50-48506
Aug. 18, 1975 Japan .................................. 50-99466
Aug. 18, 1975 Japan .................................. 50-99467

[51] Int. Cl.$^2$ ......................................... C07D 233/48
[52] U.S. Cl. ........................... 260/309.7; 260/309.5; 424/273
[58] Field of Search ..................... 260/309.5, 309.7

[56] References Cited

U.S. PATENT DOCUMENTS 3,275,643  9/1966  Lubowe .......................... 260/309.5
3,927,021  12/1975  Mecca ............................ 260/309.5

Primary Examiner—Natalie Trousof
Attorney, Agent, or Firm—Blanchard, Flynn, Thiel, Boutell & Tanis

[57] ABSTRACT

Compounds of allantoin with basic amino acids have a solubility which is from about 25 to 50 times greater than that of pure allantoin. The compounds have almost the same pharmacological effects as allantoin and the basic amino acids and they are harmless. The compounds can be used in medicines, cosmetics, creams and ointments.

6 Claims, 5 Drawing Figures

COMPOUNDS OF ALLANTOIN WITH BASIC AMINO ACIDS

BACKGROUND OF THE INVENTION

Field of the Invention

This invention relates to compounds of allantoin with basic amino acids and a process for preparing the same.

SUMMARY OF THE INVENTION

It is an object of the present invention to provide compounds of allantoin with basic amino acids.

It is another object of the present invention to provide a process for preparing allantoin/basic amino acid compounds.

It is still another object of the present invention to provide allantoin/basic amino acid compounds having a greater pharmacological effect than that of allantoin and that of the basic amino acid.

DETAILED DESCRIPTION OF THE INVENTION

The compounds obtained by combining allantoin with a basic amino acid, according to the invention, have the following formula:

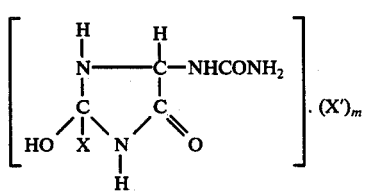

in which X is a basic amino acid radical having the formula (II) or the formula (III), X' is a basic amino acid radical of the formula (IV), and $m$ is the number of zero, one or two when X has the formula (II) and $m$ is zero when X has the formula (III).

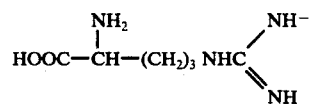

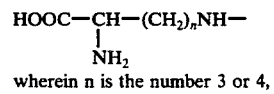

wherein n is the number 3 or 4,

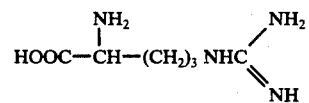

CHARACTERISTICS OF THE COMPOUNDS OF THE PRESENT INVENTION

The solubility of pure allantoin at room temperature is 0.6 wt. % in water, 1.0 wt. % in glycerol and 0.3 wt. % in 50 vol. % aqueous solution of ethyl alcohol. In contrast, the solubilities of the compounds of the present invention in the aforementioned solvents are shown in Table I. It will be understood from Table I that all compounds of the present invention can be dissolved to make present in the solution much more allantoin than can be obtained by dissolving allantoin, per se.

Table 1

| | Solubility (wt.% at 20° C) | | | |
|---|---|---|---|---|
| | | Solvent | | |
| Solute | water | 50% methyl alcohol-water solution | 50% ethyl alcohol-water solution | 50% isopropyl alcohol-water solution |
| Allantoin | 0.6 | 0.5 | 0.3 | 0.1 |
| Allatoin/arginine (1:1) compound (A) | 60.3 | 43.3 | 19.8 | 9.9 |
| Allantoin/arginine (1:2) compound | 57.2 | 39.6 | 29.7 | 22.4 |
| Allantoin/arginine (1:3) compound | 38.7 | 31.5 | 27.9 | 7.0 |
| Allantoin/ornithine compound (B) | 40.5 | 26.2 | 12.3 | 6.6 |
| Allantoin/lysine compound (C) | 30.0 | 21.7 | 9.6 | 4.8 |
| Dissolved amount of allantoin component in (A) compound | 28.2 | 20.2 | 9.4 | 4.6 |
| Dissolved amount of allantoin component in (B) component | 22.1 | 14.3 | 6.7 | 3.6 |
| Dissolved amount of allantoin component in (C) compound | 15.6 | 11.3 | 5.0 | 2.5 |

Further, a comparison of the infrared spectra of the allantoin/basic amino acid compounds was carried out.

Figure 1:
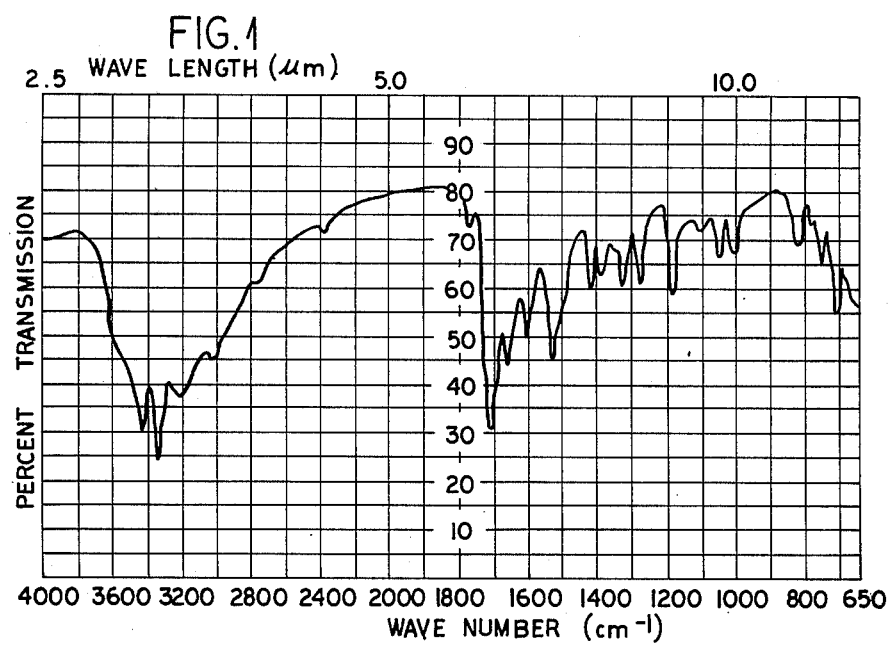
FIGS. 1, 2, 3, 4 and 5 show the infrared absorption spectra, obtained by the KBr method, of allantoin (FIG. 1), arginine (FIG. 2), the compound obtained by combining allantoin and arginine in a 1:1 mole ratio (FIG. 3), allantoin/ornithine compound (FIG. 4) and allantoin/lysine compound (FIG. 5).
Figure 2:
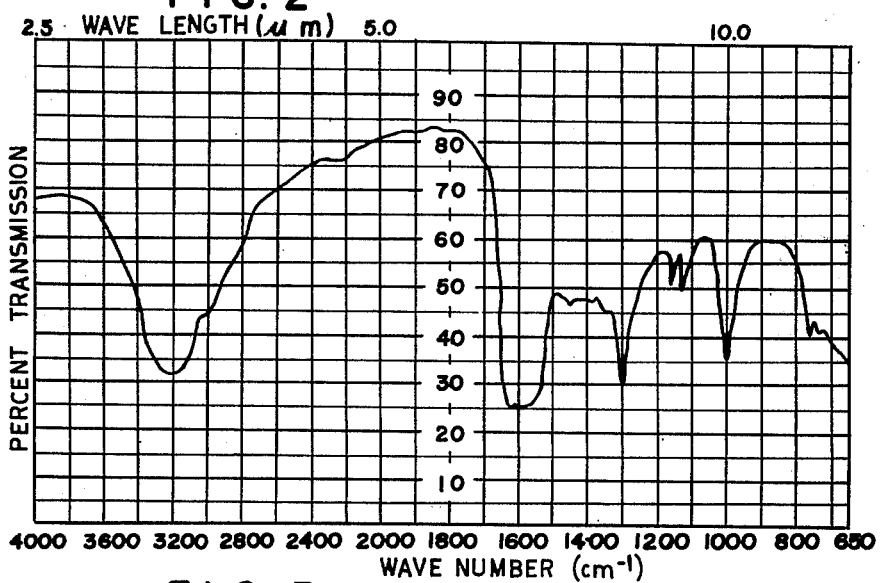
Figure 3:
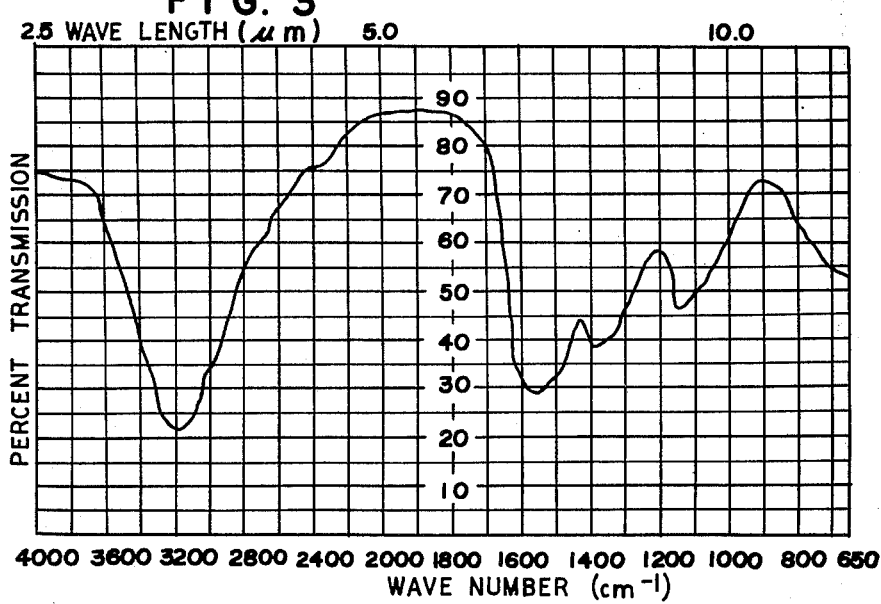

A comparison was made between the infrared adsorption spectra of allantoin shown in FIG. 1, the infrared spectra of arginine shown in FIG. 2 and the infrared spectra of the allantoin compound with arginine (1:1) shown in FIG. 3. Compared with FIG. 1 showing the spectrum of allantoin, in FIG. 3 the two peaks which are characteristics of allantoin, namely, the peaks at 1780cm$^{-1}$ and 1720 cm$^{-1}$ (—CO — NH — CO), disappeared. In other words, the peaks of cyclic imide disappeared and a peak at 1150 cm$^{-1}$, which is considered to be the one for tertiary hydroxy radical, newly appeared.

Figure 4:
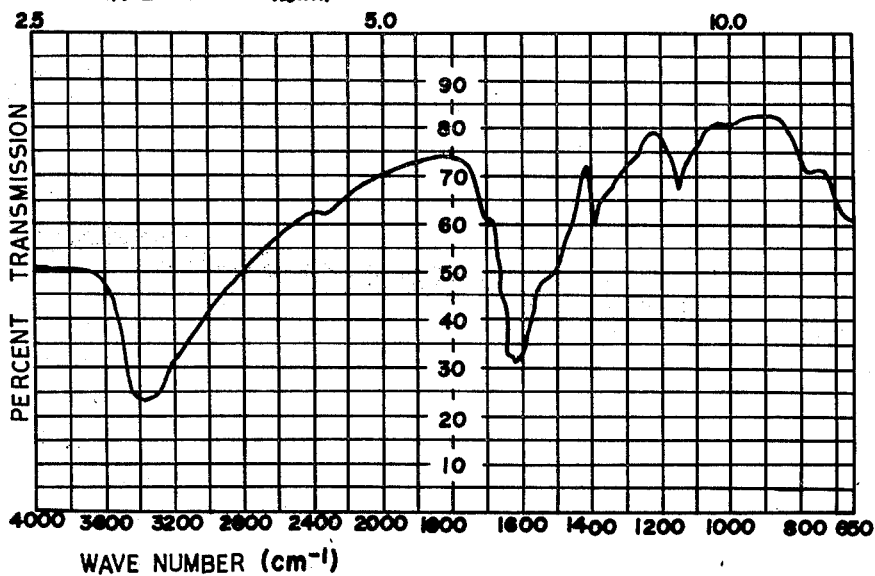
Figure 5:
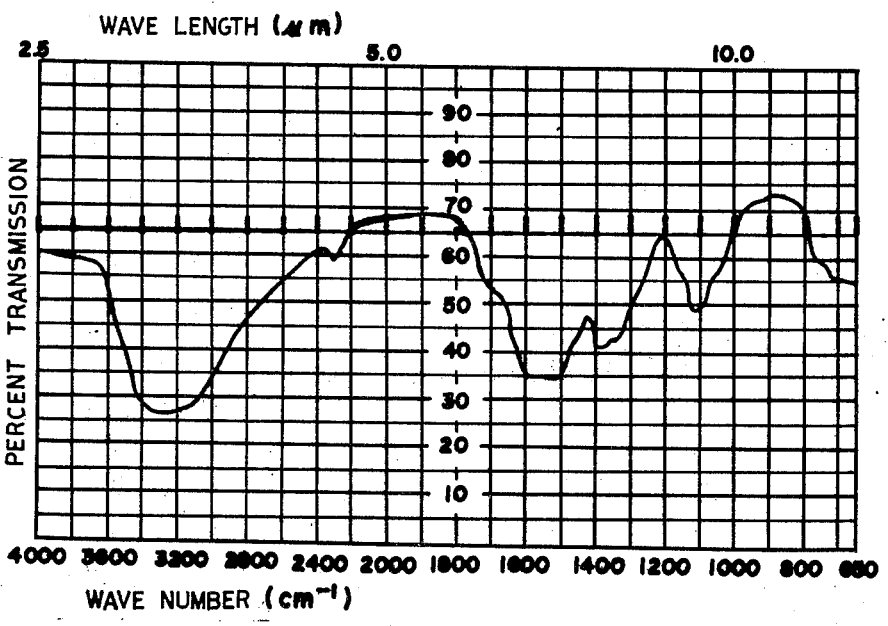

According to this procedure, comparisons were made between the infrared adsorption spectra of allantoin shown in FIG. 1 and that of the allantoin/ornithine compound shown in FIG. 4, and between the infrared adsorption spectra of allantoin shown in FIG. 1 and that of allantoin/lysine compound shown in FIG. 5. It was recognized that in the infrared spectra of these novel compounds of the present invention, the above noted characteristics adsorptions of allantoin disappeared and the peak at 1150$^{-1}$, which is considered to be the one of tertiary hydroxy radical, appeared newly, the same as in the case of the allantoin/arginine compound.

Further, differential thermal analysis of (1) mixtures of allantoin and the respective basic amino acids, and (2) the allantoin/basic amino acid compounds were carried out. It was recognized that in the chart of the mixtures (1), there appeared two peaks corresponding to the melting points of allantoin and the respective basic amino acids as shown in Table 2. In constrast, the allantoin/basic amino acid compounds exhibited only one peak which appeared at a lower temperature than the respective melting points of allantoin and the basic amino acid.

Table 2

| Material | Melting Point (° C) |
| --- | --- |
| Allantoin | 238 |
| Arginine | 228 |
| Ornithine | 140 |
| Lysine | 224 |
| Molecular Compound of allantoin with arginine | 220 |
| Molecular Compound of allantoin with ornithine | 139 (decomposed) |
| Molecular Compound of allantoin with lysine | 179 |

Referring to the pH of a saturated solution obtained by dissolving the compounds of the present invention, respectively, in water, the solution pH of allantoin/arginine molecular compound was 8.5, that of allantoin/ornithine molecular compound was 9.0 and that of allantoin/lysine compound was 8.9. When the pH of the respective saturated solutions of compounds according to the invention was adjusted, with HCl solution, to the pH value of a saturated solution of pure allantoin in water, namely 5 to 6, and even though the saturated solutions of the compounds according to the invention contain a higher concentration of allantoin than that of a saturated solution of pure allantoin, no crystals of allantoin precipitated from the respective solutions of compounds according to the invention.

Furthermore, the respective novel compounds of the present invention were subjected to qualitative analysis of α-amino acid by the nihydrin reaction. The obtained results showed that the test was positive, whereby the existence of the α-amino acid was recognized.

In view of the foregoing results, it can be concluded that the compounds of the invention are not mere mixtures of allantoin and the basic amino acids, but rather they are compounds in which allantoin and the respective basic amino acids are chemically combined.

Considering the case of the chemical reaction between allantoin and arginine, it is believed that at first, allantoin takes the enol form thereof and then the carbon atom bonded to the OH group of allantoin is combined with the guanidine group of arginine.

The chemical reaction is considered to take place mainly along the line indicated in the following reaction scheme.

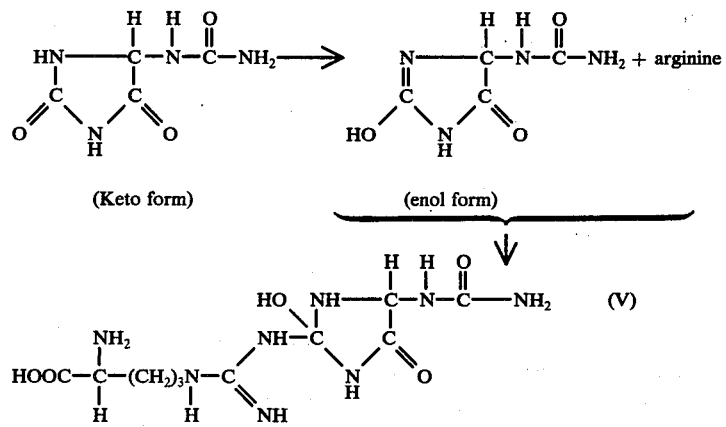

Further, when arginine is reacted with allantoin in a molar ratio (arginine:allantoin) of more than 1:1, there is obtained the addition compound of arginine and the molecular compound having the formula (V).

The formula of the thus-obtained addition compound is considered to be the following formula (VI), (VII) or a mixture of them.

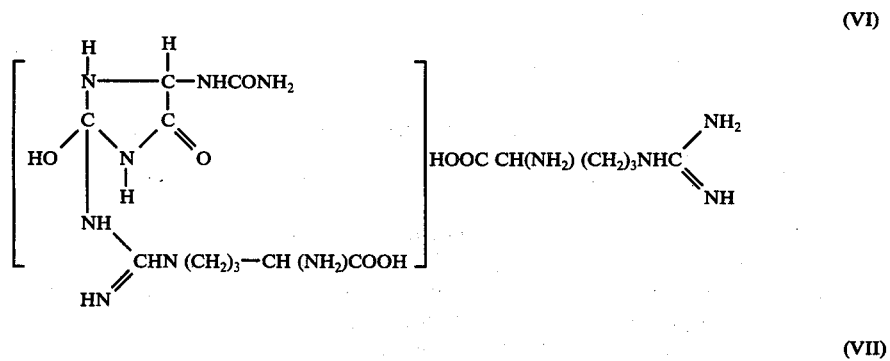

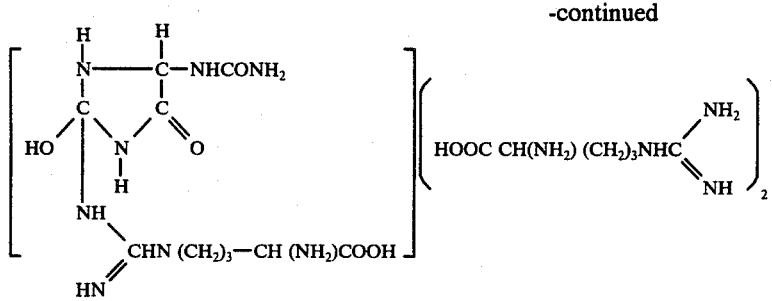

It is also considered that in the reaction between lysine and allantoin, the allantoin takes enol form which reacts with lysine according to the following reaction scheme.

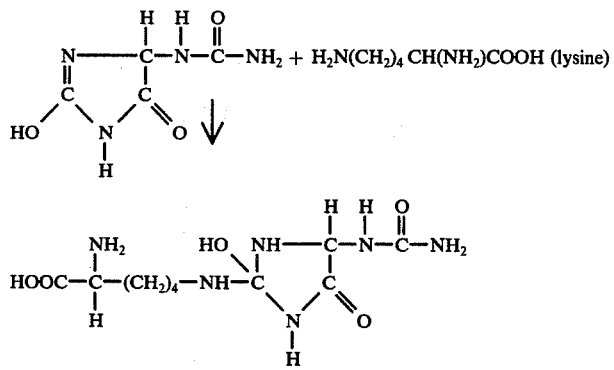

The compound of the present invention can be obtained by a process which comprises heating a mixture of allantoin and a basic amino acid in a solvent to react them and then distilling off the solvent from the reaction product.

The solvents that can be employed are water, hydrophilic solvents and mixtures thereof. The hydrophilic solvents include lower alcohols such as methyl alcohol, ethyl alcohol, isopropyl alcohol and the like, polyhydric alcohols such as ethlene glycol, glycerin, sorbitol and the like, lower ketones such as acetone and the like, and dioxane.

In view of the chemical reaction velocity and the amount of the solvent that is used, water or a mixed solvent containing water is preferred for the reaction.

The amount used of the solvent depends on the amount used of the solute, but in order to known the end point of the reaction, it is preferred that the quantity of the solvent present in the reaction system is at least sufficient to dissolve the resulting molecular compound of allantoin and the basic amino acid.

The reaction temperature is from room temperature to the boiling point of the solvent used in the reaction, but it is preferred to use a reaction temperature of more than 50° C, because the reaction velocity at room temperature is low.

The compounds of the present invention can be obtained by reacting allantoin with the respective basic amino acids in a solvent. In addition, the compounds of the invention can be obtained by using, in lieu of the basic amino acid, an addition compound of the basic amino acid with the mineral acid such as hydrochloric acid or sulphuric acid. When the basic amino acid addition compound is used, the compound of the present invention can be produced by a process which comprises the steps of adding the addition compound to a solvent which dissolves the basic amino acid of the addition compound but which does not dissolve the metal salt of the acid of the addition compound, e.g. ethyl alcohol, adding an alkali metal hydroxide or carbonate into the resulting mixture, heating the resulting mixture to react therewith thereby liberating the basic amino acid and converting the mineral acid of the addition compound into the alkali metal salt, filtering the alkali metal salt from the resultant product to obtain the basic amino acid solution, adding allantoin into said basic amino acid solution, heating the resulting mixture to effect the reaction and recovering the compound of the invention from the thus obtained reaction product.

The compound of the present invention can also be obtained by distilling off the solvent from the before mentioned basic amino acid solution to thereby obtain the basic amino acid in a syrup state, heating a mixture of allantoin and the said amino acid in a solvent to thereby effect the reaction and distilling off the solvent from the resultant product.

Furthermore, the compound of the present invention can sometimes be used according to the purpose of use thereof, in the form of a mixture of an alkali metal salt and the compound of the present invention, without purification, which mixture is obtained by adding the addition compound of the basic amino acid and the acid, the alkali metal hydroxide or carbonate to convert the acid into the alkali metal salt, and allantoin, into a solvent, heating the resulting mixture to thereby effect the reaction and distilling off the solvent from the obtained product.

Allantoin has a sedative action for allergic skin, a cell growth stimulating action, effects keratalysis of skin and has an action of eliminating necrotized tissue, etc.

However, it cannot fully display these desirable effects because its solubility in solvents is small as described in the foregoing, and the use thereof is accordingly limited.

On the contrary, the solubility of the compounds of the present invention in solvents is many times greater than that of allantoin, as shown in Table 1.

Also, comparing the dissolved amount of the allantoin component of the compounds according to the present invention and that allantoin, per se, the former is about fifteen times greater than that of allantoin, per se, and the effects of allantoin are thereby improved.

Furthermore, because the basic amino acids combined with allantoin has their own useful properties, the compounds of the present invention not only improve the effects of allantoin, but also exhibit the effects of the basic amino acid which is combined with allantoin.

For example, arginine has a detoxification and promotes an action for forming urea, ornithine removes the poisoncausing ammonia from living bodies and activates the function of the liver, and lysine has a nutritional reinforcement action.

Therefore, the novel compounds of the invention can be used in medicines, cosmetics, creams, ointments, etc., to obtain an improved effect of the allantoin moiety and maintaining the effects of the basic amino acid.

PREFERRED EMBODIMENTS OF THE INVENTION

EXAMPLE 1

200 ml of water, 15.8 g of allantoin and 17.4 g of arginine were added into a four opening flask which was equipped with a mechanical stirrer, a thermometer and a reflux condenser. The resulting mixture was heated to 80° C while being stirred and was kept at this temperature for two hours. Then, water was distilled from the reaction product under reduced pressure to obtain 33 g of white powder (yield : 99 wt. % of the theoretical amount).

The results of the infrared adsorption spectra and differential thermal analysis thereof showed that the product was the molecular compound of allantoin with arginine.

EXAMPLE 2

1.000 g of methyl alcohol, 1.58 g of allantoin and 1.74 g of arginine were added into the reaction apparatus used in Example 1.

The resulting mixture was reacted, with reflux of the solvent, for five hours. After the reaction was over, methyl alcohol was distilled off from the resultant product to obtain 3.2 g of white powder (yield: 96% of the theoretical amount).

The results of the infrared adsorption spectra and the differential thermal anaylsis thereof showed that it was allantoin compound with arginine.

EXAMPLE 3

A mixture of 150 ml of water, 100 g of ethyl alcohol, 15.8 g of allantoin, and 17.4 g of arginine was reacted at 75° for 3 hours in a manner similar to that of Example 1. After the reaction was over, the solvent was distilled off under reduced pressure to obtain 32. 5 g of white powder (yield: 98% of the theoretical amount).

The results of the infrared absorption spectra and the differential thermal analysis thereof showed that it was allantoin compound with argine.

EXAMPLE 4

A mixture of 500 g of glycerin, 15.8 g of allantoin and 17.4 g of arginine was reacted at 100° C for ten hours in a manner similar to that of Example 1 to obtain a transparent solution containing 6.2 wt. % of allantoin compound with arginine.

EXAMPLE 5

Into the reaction apparatus used in Example 1, 160 g of ethyl alcohol, 16.8 g of ornithine hydrochloride and 5.6 g of potassium hydroxide were added. The resulting mixture was reacted for 3 hours, refluxing the solvent, while being stirred. After the reaction was over, the resultant product was cooled to room temperature and then the by-product potassium chloride was filtered off. Then the solvent was distilled off from the resultant product under reduced pressure to obtain 13.0 g of ornithine in a syrupy state.

This ornithine syrup, 15.8 g of allantoin and 150 ml of water were added into the apparatus again. The resulting mixture was heated at 75° C, for 2 hours, while being stirred. After the reaction was over, the water was distilled off from the resultant product under reduced pressure to obtain 27.5 g of pale yellow powder (yield: 95% of the theoretical amount).

The results of the infrared absorption analysis and the X-ray analysis thereof showed that the powder was allantoin compound with ornithine.

EXAMPLE 6

A mixture of 80 g of isopropyl alcohol, 8.4 g of ornithine hydrochloride and 2.0 g of sodium hydroxide were reacted for 3 hours according to the same procedure as that described in Example 5. The resultant product was cooled to room temperature and the by-product sodium chloride was filtered off therefrom. The filtrate thereof was charged again into the apparatus and was reacted with 7.9 g of allantoin for 5 hours, refluxing the solvent.

After the reaction was over, the resultant product was cooled to room temperature and was filtered to obtain 13.3 g of pale yellow powder (yield: 92% of the theoretical amount).

The results of the infrared absorption spectra and the X-ray analysis thereof showed that the powder was allantoin compound with ornithine.

EXAMPLE 7

150 ml of water, 16.8 g of ornithine hydrochloride, 15.8 g of allantoin and 4.0 g of sodium hydroxide were charged into the apparatus. The resulting mixture was heated to 80° C while being stirred and was kept for 2 hours.

After the reaction was over, water was distilled off from the resultant product to obtain 34.7 g of pale yellow powder.

The results of the infrared absorption spectra and the X-ray analysis thereof showed that the powder was a mixture of allantoin compound with ornithine and sodium chloride.

EXAMPLE 8

150 ml of water, 15.8 g of allantoin and 29.2 g of 50 wt.% aqueous solution of lysine, were charged into the apparatus used in Example 1. The resulting mixture was heated to 80° C while being stirred and was kept for 2 hours.

After the reaction was over, water was distilled off under reduced pressure from the resultant product to obtain 30 g of pale yellow powder (yield: 99% of theoretical amount).

The results of the infrared absorption spectra and the X-ray analysis thereof showed that the powder was molecular compound of allantoin with lysine.

EXAMPLE 9

A mixture of 150 ml of water, 100 g of methyl alcohol, 15.8 g of allantoin and 29.2 g of 50 wt.% aqueous solution of lysine was reacted at 75° C for 3 hours in a manner similar to that of Example 1. After the reaction was over, the solvent was distilled off under reduced pressure from the thus obtained product, whereby 29.6 g of pale yellow powder was obtained (yield: 98% of the theoretical amount).

The results of the infrared absorption spectra and the X-ray analysis thereof showed that the powder was allantoin compound with lysine.

EXAMPLE 10

Into the reaction apparatus used in Example 1, 160 g of ethyl alcohol, 18.3 g of lysine hydrochloride and 4.0 g of sodium hydroxide were charged. The resulting mixture was heated, refluxing the solvent, while being stirred, and was kept for 3 hours. The resultant product was cooled to room temperature and the by-product sodium chloride was filtered off therefrom. The solvent was distilled off from the obtained product to obtain 14.3 g of lysine in a syrup state. The lysine obtained, 15.8 g of allantoin and 150 ml of water were charged into the apparatus.

The resulting mixture was heated to 80° C while being stirred and was kept for 2 hours.

After the reaction was over, water was distilled off from the resultant product, whereby 28.8 g of pale yellow powder were obtained (yield: 95% of the theoretical amount).

The results of the infrared absorption spectra and the X-ray analysis thereof showed that the powder was allantoin molecular compound with lysine.

EXAMPLE 11

A mixture of 320 g of ethyl alcohol, 36.6 g of lysine hydrochloride and 8.0 g of sodium hydroxide was reacted for 3 hours in a manner similar to that of Example 3. The obtained products were cooled to room temperature and the byproduct sodium chloride was filtered off from them.

350 g of the filtrate and 31.6 g of allantoin were charged into the apparatus. The mixture was reacted for 3 hours, while refluxing the solvent. The resultant product was cooled to room temperature and subjected to filtration to obtain 56.4 g of pale yellow powder.

The results of the infrared absorption spectra and the X-ray analysis thereof showed that the powder was allantoin compound with lysine.

EXAMPLE 12

150 ml of water, 18.3 g of lysine hydrochloride, 15.8 g of allantoin and 8.4 g of sodium bicarbonate were charged into the reaction apparatus used in Example 1.

The resulted mixture was heated to 80° C while being stirred and was kept for 2 hours.

After the reaction was over, water was distilled off from the resultant products to obtain 36.2 g of pale yellow powder.

The results of the infrared absorption spectra and the X-ray analysis thereof showed that the powder was a mixture of allantoin molecular compound with lysine and sodium chloride.

The embodiments of the invention in which an exclusive property or privilege is claimed are defined as follows:

1. A compound of the formula

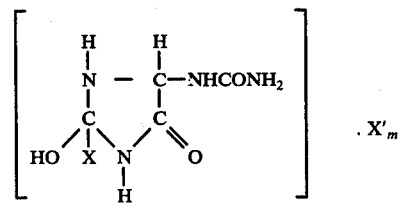

in which X is a basic amino acid radical having the formula (II) or the formula (III), X' is a basic amino acid radical having the formula (IV), m is zero, one or two when X is the formula (II) and m is zero when X is the formula (III)

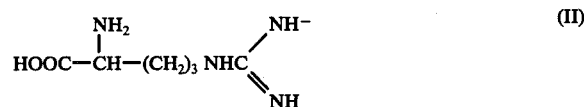

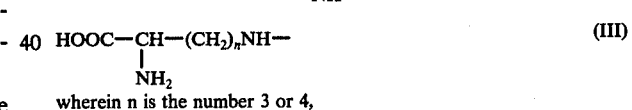

wherein n is the number 3 or 4,

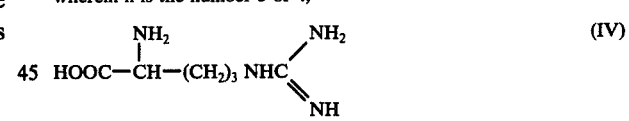

2. A compound according to claim 1, in which m is zero, and X has the formula (II), namely, allantoin/arginine (1:1) compound.

3. A compound according to claim 1, in which m is one and X has the formula (II), namely, allantoin/arginine (1:2) compound.

4. A compound according to claim 1, in which m is two and X has the formula (II), namely, allantoin/arginine (1:3) compound.

5. A compound according to claim 1, in which X has the formula (III), n is 3 and m is zero, namely, allantoin/ornithine (1:1) compound.

6. A compound according to claim 1, in which X has the formula (III), n is 4 and m is zero, namely, allantoin/lysine (1:1) compound.

* * * * *